March 7, 1967 R. V. LINDQUIST Plant Pat. 2,725
ROSE PLANT
Filed Feb. 21, 1966
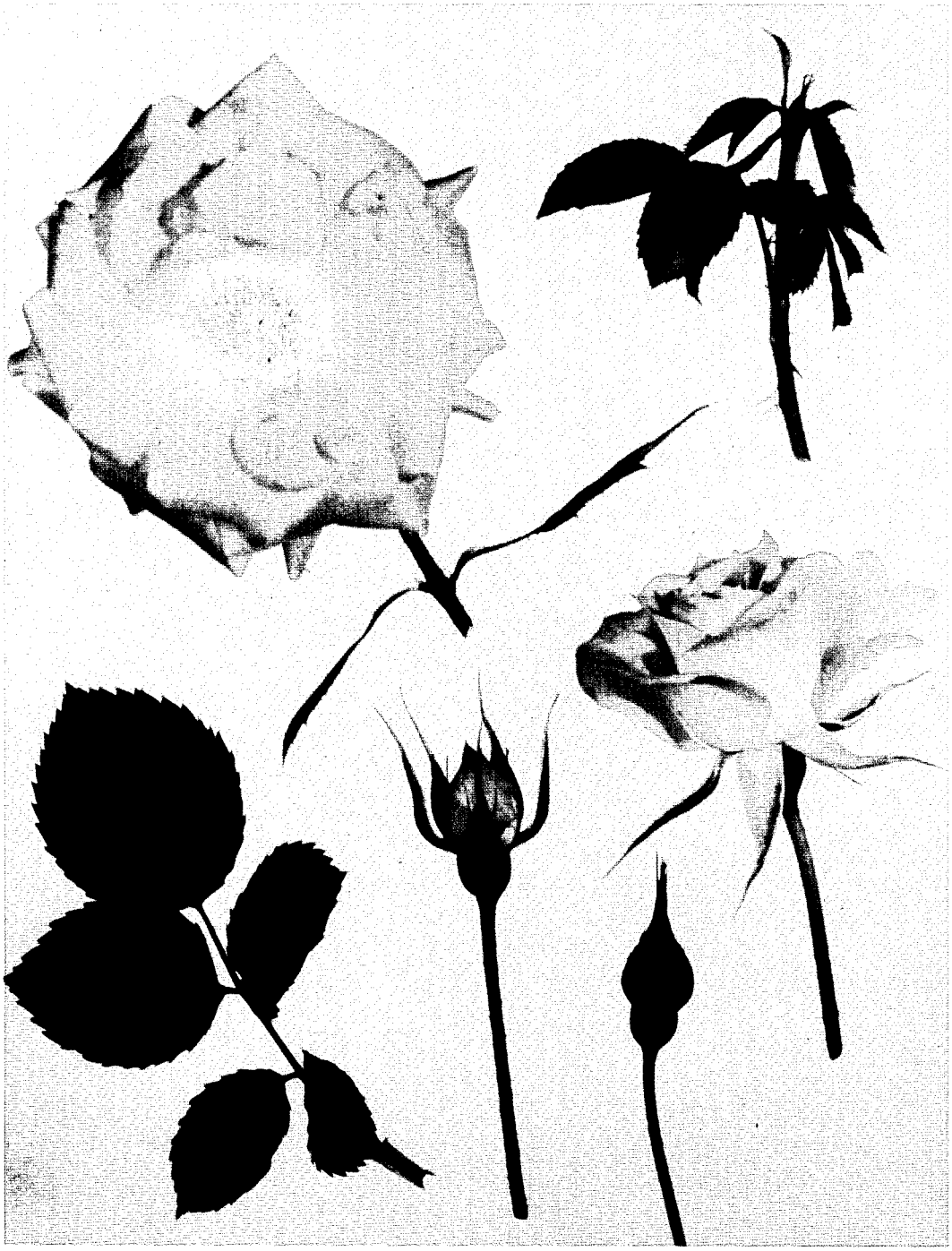
Inventor.
R. V. Lindquist
By: Robb & Robb
Attorneys.

United States Patent Office

Plant Pat. 2,725
Patented Mar. 7, 1967

2,725
ROSE PLANT

Robert V. Lindquist, Hemet, Calif., assignor to Hemet Wholesale, Hemet, Calif., a partnership

Filed Feb. 21, 1966, Ser. No. 529,163
1 Claim. (Cl. Plt.—22)

The present invention relates to a new and distinct variety of rose plant of the floribunda class, which was originated by me by crossing an unnamed and unpatented seedling of "Pinkie" (Plant Patent No. 712) × "Independence" (Plant Patent No. 1,036) with the variety "Circus" (Plant Patent No. 1,382).

As the result of this breeding, I have produced a new rose variety which is particularly characterized as to novelty by the unique combination of the following features which are outstanding therein and which distinguish it from its parents, as well as from all other varieties of which I am aware:

(1) A bushy and low-growing plant habit which is ideal for group plantings and borders;

(2) Attractive dark green and leathery foliage;

(3) Urn-shaped buds;

(4) Double flowers of high-centered to open form and which are borne in good clusters;

(5) Distinctive and attractive bi-colored flowers which are yellow at their base, shading to bright orange-red over the remainder of each flower; and (6) A moderate tea fragrance of the flowers.

Assexual reproduction of my new variety by budding, as performed at Hemet, California, shows that the foregoing characteristics and distinctions come true to form and are established and transmitted through succeeding propagations.

The accompanying drawing shows typical specimens of the vegetative growth and flowers of my new variety in different stages of development as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "W") and Ridgway's Color Standards and Nomenclature (hereinafter abbreviated as "R"), as indicated:

Type: Hardy; bush; outdoor; seedling; for cut flowers and for garden decoration.

Class: Floribunda.

Breeding: Seedling.

*Seed parent.*—An unnamed seedling of "Pinkie" × "Independence."

*Pollen parent.*—"Circus."

Propogation: Holds its distinguishing characteristics through succeeding propagations by budding.

*Flower*

Locality where grown and observed: Hemet, California.

Flowers borne: Sometimes singly, but usually 3 or more to stem; in irregular clusters; on strong stems of medium length.

Quantity of bloom: Free, both outdoors and in greenhouse.

Continuity: Continuous during growing season.

Fragrance: Moderate. Nature—tea.

Bud:

*Peduncle.*—Average length; average caliper; erect; moderately smooth; some gland-tipped cilia; few prickles. Color—near Lettuce Green, Plate V (R).

*Before calyx breaks.*—Size—medium. Form—medium length; pointed; with a conspicuous neck; with foliaceous appendages; few gland-tipped cilia; usually with slender bristle-like foliaceous parts extending beyond the tip of the bud equal to ½ or more of its length.

*As calyx breaks.*—Color—near Canary Yellow, Plate 2/1, page 2 (W) at base, fusing into varying shades of Scarlet, Plate 19/1, page 19 (W) toward middle and outer tip of petal.

*Sepals.*—Inner surface—with fine, wooly tomentum; margins with foliaceous appendages; lined with gland-tipped cilia and hairs.

*As first petal opens.*—Size—average. Form—medium length; urn-shaped. Color: outside—near Scarlet, Plate 19/1, page 19 (W), slightly veined with near Canary Yellow, Plate 2/1, page 2 (W), and with base of near Canary Yellow, Plate 2/1, page 2 (W); inside—near Single Red, Plate 719, page 93 (W), with base of near Canary Yellow, Plate 2/1, page 2 (W).

*Opening.*—Opens up well; is not retarded by cold, hot, wet or dry weather.

Bloom:

*Size (when fully open).*—Average; from 2½ inches to 3 inches.

*Petalage.*—Semi-double; from 25 to 30 petals, plus 3 or 4 petaloids; arranged irregularly.

*Form.*—High-centered at first, but becoming open to high-centered; petals being at first somewhat tightly cupped, with tips reflexed outward, but later becoming somewhat more loosely cupped, with tips reflexed outward, at maturity.

Petals:

*Texture.*—Medium thickness; moderately leathery; soft.

*Appearance.* — Inside — slightly satiny. Outside—slightly satiny.

*Shape.*—Outside—round, with apex pointed. Intermediate—round, with apex pointed. Inside—nearly round, with apex pointed, and some with 1 notch.

This description of a newly opened flower was made from a rose grown in a greenhouse during the month of January at Hemet, California:

*Color.*—Outer petal: outside surface—near Geranium Lake, Plate 20/1, page 20 (W) at outer edge of petal, shading into near Chinese Yellow, Plate 606/1, page 68 (W) toward base, with base near Lemon Yellow, Plate 4/1, page 4 (W); inside surface—near Scarlet, Plate 19, page 19 (W), with some shading of near Chinese Yellow, Plate 606, page 68 (W) toward base, and with base near Lemon Yellow, Plate 4/1, page 4 (W). Intermediate petal: outside surface—near Vermilion, Plate 18/1, page 18 (W) at outer edge, veined and shading into near Chinese Yellow, Plate 606, page 68 (W), with base near Lemon Yellow, Plate 4, page 4 (W); inside surface—near Dutch Vermilion, Plate 717/1, page 156 (W), with base near Lemon Yellow, Plate 4, page 4 (W). Inner petal: outside surface—outer edge of petal near Fire Red, Plate 15, page 15 (W), with shadings of near Chinese Yellow, Plate 606, page 68 (W) toward base, and with base near Lemon Yellow, Plate 4, page 4 (W); inside surface—near Fire Red, Plate 15, page 15 (W), with base near Lemon Yellow, Plate 4/1, page 4 (W).

This description was made from a rose that was open for three days in a greenhouse during the month of January at Hemet, California:

*Color.*—Outer pedal: outside surface—near Carmine, Plate 21/1, page 21 (W), slightly veined with near Canary Yellow, Plate 2/3, page 2 (W), with base near Canary Yellow, Plate 2/2, page 2 (W); inside surface—near Carmine, Plate 21/1, page 21 (W), shading into near Canary Yellow, Plate 2/1, page 2 (W) at base. Inner petal: outside surface—near Carmine, Plate 21/2, page 21 (W) at outer edge of pedal, shading into near Carmine, Plate 21/3, page 21 (W) toward center of petal, with lower portion of petal near Lemon Yellow, Plate 4/3, page 4 (W), and with base near Lemon Yellow, Plate 4/1, page 4 (W); inside surface—near Carmine, Plate 21/2, page 21 (W), with base near Lemon Yellow, Plate 4/1, page 4 (W).

*General color effect.*—Newly opened flower—near Scarlet, Plate 19, page 19 (W). 3 days open—near Carmine, Plate 21/1, page 21 (W).

*Behavior.*—Drop off cleanly.

*Flower longevity.*—On bush in garden—4 or 5 days in June. Cut roses grown outdoors and kept at living-room temperatures—5 or 6 days in June. Cut roses grown in greenhouse and kept at living-room temperatures—5 or 6 days in January.

*Reproductive organs*

Stamens: Average number; arranged regularly about pistils.

Filaments: Medium length; most with anthers.

Anthers: Medium size; all open approximately at once. Color: upper side—near Orange Ochre, Plate 07, page 101 (W); under side—near Yellow Ochre, Plate 07/1, page 101 (W).

Pollen: Moderate abundance. Color — near Spanish Orange, Plate 010/1, page 103 (W).

Pistils: Average number (approximately 80).

Styles: Uneven; average length; average caliper; somewhat bunched.

Stigma: Color—near Buff Yellow, Plate IV (R).

Ovaries: Usually all enclosed in calyx.

Hips: Average length; globular; with inconspicuous neck; moderately smooth; walls thick and fleshy. Color—near Indian Orange, Plate 713, page 155 (W).

Sepals: Falling soon; medium length; spear-shaped; recurved. Color: inside—near Biscay Green, Plate XVII (R); outside—near Lettuce Green, Plate V (R).

Seeds: Few (from 10 to 18 in number); from small to medium size.

*Plant*

Foliage:

*Leaves.*—Compound of usually 5–7 leaflets; normal abudance; from medium size to large; moderately heavy; somewhat leathery and semi-glossy.

*Leaflets.*—Shape — oval. Apex — acute. Base—round. Margin—irregularly serrate.

*Color.*—Mature: upper surface—near Dull Yellow Green, Plate XXXII (R); under surface—near Light Elm Green, Plate XVII (R). Young: upper surface—near Spinach Green, Plate V (R); under surface—near Light Elm Green, Plate XVII (R).

*Rachis (the supporting stem of the compound leaf).*—Average size. Upper side—grooved; with some stipitate glands on edges; prickly. Under side—prickly; with stipitate glands.

*Stipules.*— Medium length; narrow; with short points turning out at an angle of more than 45°.

*Disease resistance.*—Mildly subject to mildew, as determined by comparison with other varieties grown under comparable cultural conditions at Hemet, California.

Growth:

*Habit.*—Bushy; much-branched.

*Growth.*—Free; vigorous.

*Canes.*—Medium caliper.

*Main stems.*—Color—near Cerro Green, Plate V (R). Large prickles—several; medium length; curved slightly downward; with narrow base of medium length; color—near Russet, Plate XV (R). Small prickles—several; color—near Sayal Brown, Plate XXIX (R). Hairs—none.

*Branches.*—Color—near Oil Green, Plate V (R). Large prickles—several; medium length; curved slightly downward; with base of medium length; color—near Sayal Brown, Plate XXIX (R). Small prickles—several; color—near Tawny-Olive, Plate XXIX (R). Hairs—none.

*New shoots.*—Color—near Spinach Green, Plate V (R), with shades of Dark Corinthian Purple, Plate XXXVIII (R). Large prickles — few; medium length; almost straight; with narrow base of medium length; color—near Deep Corinthian Red, Plate XXVII (R) at base, tipped with near Kildare Green, Plate XXXI (R). Small prickles—few; color—near Kildare Green, Plate XXXI (R). Hairs—none.

I claim:

A new and distinct variety of rose plant of the floribunda class, substantially as herein shown and described, characterized particularly as to novelty by the unique combination of a bushy and low-growing plant habit which is ideal for group plantings and borders, attractive dark green and leathery foliage, urn-shaped buds, double flowers of high-centered to open form and which are borne in good clusters, distinctive and attractive bi-colored flowers which are yellow at their base, shading to bright orange-red over the remainder of each flower; and a moderate tea fragrance of the flowers.

No references cited.

ABRAHAM G. STONE, *Primary Examiner.*

ROBERT E. BAGWILL, *Examiner.*